(12) United States Patent
Moody et al.

(10) Patent No.: US 9,024,025 B2
(45) Date of Patent: May 5, 2015

(54) PROCESS AND INTERMEDIATE COMPOUNDS USEFUL IN THE PREPARATION OF STATINS, PARTICULARLY ROSUVASTATIN

(71) Applicant: Redx Pharma Limited, Manchester (GB)

(72) Inventors: David J. Moody, Fife (GB); Jonathan W. Wiffen, Craigavon (GB)

(73) Assignee: Redx Pharma Limited, Manchester (GB)

( * ) Notice: Subject to any disclaimer, the term of this patent is extended or adjusted under 35 U.S.C. 154(b) by 0 days.

(21) Appl. No.: 14/225,018

(22) Filed: Mar. 25, 2014

(65) Prior Publication Data

US 2014/0316135 A1    Oct. 23, 2014

Related U.S. Application Data

(62) Division of application No. 10/594,380, filed as application No. PCT/GB2005/001099 on Mar. 23, 2005, now Pat. No. 8,703,945.

(30) Foreign Application Priority Data

Mar. 26, 2004 (GB) .................................. 0406757.5

(51) Int. Cl.

| | |
|---|---|
| *C07D 405/06* | (2006.01) |
| *C07D 309/10* | (2006.01) |
| *C07D 309/30* | (2006.01) |
| *A61K 31/506* | (2006.01) |
| *A61P 3/06* | (2006.01) |

(52) U.S. Cl.
CPC ............ *C07D 405/06* (2013.01); *C07D 309/10* (2013.01); *C07D 309/30* (2013.01)

(58) Field of Classification Search
CPC ... C07D 309/10; C07D 309/30; C07D 405/06
USPC ........................................................ 544/330
See application file for complete search history.

(56) References Cited

U.S. PATENT DOCUMENTS

| | | |
|---|---|---|
| 4,474,971 A | 10/1984 | Wareing |
| 4,625,039 A | 11/1986 | Jewell, Jr. et al. |
| 4,677,211 A | 6/1987 | Jewell, Jr. et al. |
| 8,703,945 B2 * | 4/2014 | Moody et al. ................ 544/330 |

| | | |
|---|---|---|
| 2003/0232989 A1 | 12/2003 | Antons et al. |
| 2004/0006097 A1 | 1/2004 | Hill et al. |
| 2007/0093660 A1 | 4/2007 | Tararov et al. |

FOREIGN PATENT DOCUMENTS

| | | |
|---|---|---|
| WO | WO-01/85702 A1 | 11/2001 |
| WO | WO-03/026573 A2 | 4/2003 |
| WO | WO-2005/030758 A1 | 4/2005 |
| WO | WO-2005/040134 A1 | 5/2005 |
| WO | WO-2005/047276 A2 | 5/2005 |

OTHER PUBLICATIONS

Barnes, N.J. et al., "The Synthesis of Optically Active Tetrahydropyrans by the Addition of a Stabilised Wittig Reagent to Pyranose Sugars," J. Chem. Soc., Chem. Commun., (19):1292-1294 (1985).

Barth, M. et al., "Towards a New Type of HMG-CoA Reductase Inhibitor", *Tetrahedron*, 46(19):6731-6740 (Elsevier Science Publishers, Amsterdam, NL, 1990).

Beck, G. et al., "Synthesis and Biological Activity of New HMG-CoA Reductase Inhibitors. 1. Lactones of Pyridine- and Pyrimidine-Substituted 3,5-Dihydroxy-6-heptenoic(-heptanoic) Acids", *J. Med. Chem.*, 33(1):52-60 (American Chemical Society, Washington, DC, 1990).

(Continued)

*Primary Examiner* — Venkataraman Balasubramanian
(74) *Attorney, Agent, or Firm* — Dana M. Gordon; Foley Hoag LLP

(57) ABSTRACT

Provided are a compound of formula (5) and a process for its preparation

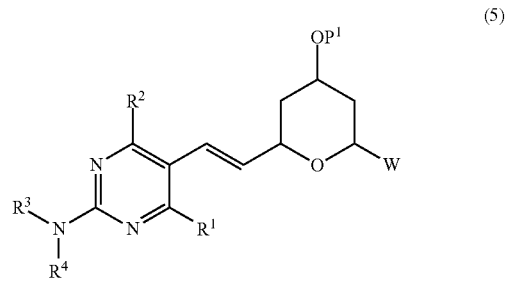

(5)

wherein: $R^1$ represents an alkyl group; $R^2$ represents an aryl group; $R^3$ represents a protecting group or an alkyl group; $R^4$ represents a protecting group or a $SO_2R^5$ group where $R^5$ is an alkyl group; $R^6$ represents $(PR^7R^8)^+X^-$ or $P(=O)R^7R^8$ in which X is an anion and $R^7$ and $R^8$ each independently is an alkyl, aryl, alkoxy, or aryloxy group; $P^1$ represents hydrogen or a protecting group; and W represents $=O$ or $OP^2$, in which $P^2$ represents hydrogen or a protecting group.

21 Claims, No Drawings

(56) References Cited

OTHER PUBLICATIONS

"Chapter 27. Reactions of Enolates with Aldehydes and Ketones: the Aldol Reaction," *Organic Chemistry*, eds. Clayden, Greeves, Warren, and Wothers, Oxford University Press, 2001, pp. 692-693.

"Chapter 28. Acylation at Carbon", *Organic Chemistry*, eds. Clayden, Greeves, Warren, and Wothers, Oxford University Press, 2001, pp. 723-724.

Durand-Reville, T. et al., "Highly Selective Entry to the Azadirachtin Skeleton via a Claisen Rearrangement/Radical Cyclization Sequence", *Organic Letters*, 4(22):3847-3850 (2002).

Paterson, I. et al., "Phorboxazole B synthetic studies: construction of C(1-32) and C(33-46) subtargets", *Organic & Biomolecular Chemistry*, 2(20):3026-3038 (2004).

Rosen, T. et al., "Synthetic and Biological Studies of Compactin and Related Compounds. 2. Synthesis of the Lactone Moiety of Compactin", *J. Org. Chem.*, 49:3994-4003 (American Chemical Society, Easton, US, Oct. 19, 1994).

Yang, Y.-L. et al., "Mevinic Acids and Analogues: Preparation of a Key Chiral Intermediate", *Tetrahedron Letters*, 23(42):4305-4308 (Pergamon Press Ltd., Great Britain, 1982).

Wade, P.A. et al., "A Useful Route to Optically Active 4-Oxygenated 4,5-Dihydroisoxazoles", *J. Org. Chem.*, 59:7199-7200 (1994).

Wiberg, K.B. et al., "Lactones. 3. A Comparison of the Basicities of Lactones and Esters," *J. Am. Chem. Soc.* 113:7705-7709 (1991).

International Search Report from PCT/GB2005/001099, dated Sep. 16, 2005.

\* cited by examiner

PROCESS AND INTERMEDIATE COMPOUNDS USEFUL IN THE PREPARATION OF STATINS, PARTICULARLY ROSUVASTATIN

RELATED APPLICATIONS

This application is a divisional of U.S. patent application Ser. No. 10/594,380, having a 371(c) date of Jul. 29, 2008, which is the U.S. National Phase of PCT/GB2005/001099, having an international filing date of Mar. 23, 2005, which claims the benefit of priority to Great Britain Patent Application No. 0406757.5, filed Mar. 26, 2004.

The present invention concerns a process and intermediate compounds useful in the preparation of statins, particularly Rosuvastatin.

According to the present invention, there is provided a process for the preparation of a compound of formula (7):

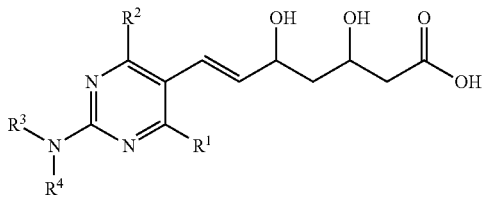

wherein
$R^1$ represents an alkyl group, such as a $C_{1-6}$ alkyl group, and preferably an isopropyl group;
$R^2$ represents an aryl group, preferably a 4-fluorophenyl group;
$R^3$ represents hydrogen, a protecting group or an alkyl group, such as a $C_{1-6}$ alkyl group, and preferably a methyl group; and
$R^4$ represents hydrogen, a protecting group or a $SO_2R^5$ group where $R^5$ is an alkyl group, such as a $C_{1-6}$ alkyl group, and preferably a methyl group,
which comprises
a) hydroxylating a compound of formula (1):

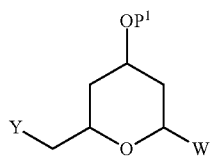

wherein Y represents a halo group, preferably Cl or Br; $P^1$ represents hydrogen or a protecting group, and W represents =O or $OP^2$, in which $P^2$ represents hydrogen or a protecting group,
to give a compound of formula (2):

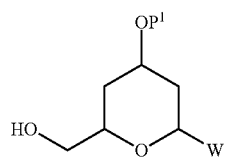

b) oxidising the compound of formula (2) to give a compound of formula (3):

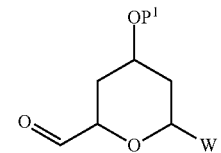

c) coupling the compound of formula (3) with a compound of formula (4):

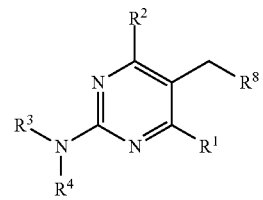

wherein $R^3$ represents a protecting group or an alkyl group, such as a $C_{1-6}$ alkyl group, and preferably a methyl group; $R^4$ represents a protecting group or a $SO_2R^5$ group where $R^8$ is an alkyl group, such as a $C_{1-6}$ alkyl group, and preferably a methyl group; and $R^6$ represents $(PR^7R^8)^+X^-$ or $P(=O)R^7R^8$ in which X is an anion and $R^7$ and $R^8$ each independently is an alkyl, aryl, alkoxy or aryloxy group, preferably a phenyl group,
to give a compound of formula (5):

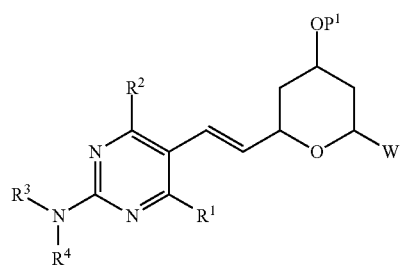

wherein $R^3$ represents a protecting group or an alkyl group, such as a $C_{1-6}$ alkyl group, and preferably a methyl group; and $R^4$ represents a protecting group or a $SO_2R^6$ group where $R^5$ is an alkyl group, such as a $C_{1-6}$ alkyl group, and preferably a methyl group,
d) when W represents $-OP^2$, removing any $P^2$ protecting group and oxidising the compound of formula (5) to give a compound of formula (6):

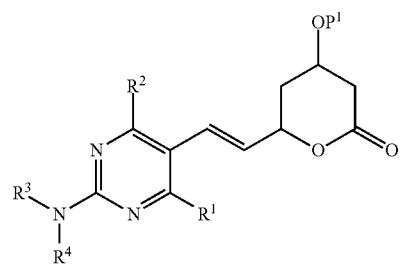

and
e) subjecting the compound of formula (5) when W represents =O, or compound of formula (6) to ring-opening, removal of any P¹ protecting groups, and optionally removing any additional protecting groups to give a compound of formula (7).

In step (e), any P¹ protecting groups and any additional protecting groups may be removed individually or together and prior to ring opening, during ring opening or after ring opening of the compounds of formula (5) or (6).

Preferably, in steps (a) to (c), W is $OP^2$ for the compounds of formula (1), (2), (3) and (5).

Protecting groups which may be represented by $P^1$ and $P^2$ include alcohol protecting groups, examples of which are well known in the art. Particular examples include tetrahydropyranyl, benzyl and methyl groups, and optionally substituted variants thereof. Substituents may advantageously be used to modify the ease of introduction or removal of the protecting group. Preferred protecting groups are silyl groups, for example triaryl- and especially trialkylsilyl groups. Especially preferred examples are trimethylsilyl, t-butyldimethylsilyl and t-butyldiphenylsilyl groups.

Protecting groups which may be represented by $P^1$ and $P^2$ may be the same or different. When the protecting groups $P^1$ and $P^2$ are different, advantageously this may allow for the selective removal of only $P^1$ or $P^2$. Preferably, when the protecting groups $P^1$ and $P^2$ are different, $P^1$ is a tetrahydropyranyl, benzyl, or silyl group and $P^2$ is a methyl group. More preferably, when the protecting groups $P^1$ and $P^2$ are different, $P^1$ is a benzyl, or silyl group and $P^2$ is a methyl group.

Protecting groups which may be represented by $R^3$ and $R^4$ include amine protecting groups, examples of which are well known in the art. Particular examples include benzyl groups, carbamates (such as CBZ, Boc, Fmoc), phosphate, thiophosphate, silyl groups and, when $R^3$ and $R^4$ together are a single protecting group, an imine group.

Hydroxylation of compounds of formula (1) can be achieved by methods known in the art for displacing a halo group with a hydroxide source. Preferably, the process comprises contacting the compound of formula (1) with a source of hydroxide. Hydroxide sources include hydroxide salts, especially ammonium or alkali metal hydroxides, particularly lithium, sodium or potassium hydroxide, and various aqueous media such as water in the presence of basic media such as N-methylpryrrolidinone, HMPA, $Al_2O_3$, $CaCO_3$, $Na_2CO_3$, $K_2CO_3$ or $KO_2$/18-crown-6, silver salts such as $AgNO_3$ or $Ag_2O$, or oxidants such perbenzioc acid. A particularly preferred process comprises contacting the compound of formula (1) with 5 molar equivalents of KOH in the presence of dimethylsulfoxide solvent at a temperature of, for example, about 50° C.

Alternatively, hydroxylation may be achieved by first displacing the halogen with a leaving group such as acetate, triflate or sulphate optionally in the presence of a silver salt, then displacing the leaving group with a hydroxide source. A particularly preferred process comprises contacting the compound of formula (1) with 3 molar equivalents of NaOAc in the presence of dimethylformamide solvent and tetra-n-butylammonium chloride at a temperature of, for example, about 100° C., isolating the acetyl compound and contacting with potassium carbonate in the presence of methanol solvent and at a temperature of, for example, about 0° C.

Oxidation of compounds of formula (2) can be achieved using oxidation systems known in the art for the oxidation of alcohols, especially those known in the art for the oxidation of primary alcohols. Examples include oxidation with Dess-Martin periodinane, bromine, Swern oxidation or various metal based oxidations such as Fetizon reagent, manganate based reagents, and chromate based reagents such as Collins reagent. Swern oxidation is preferred. When Swern oxidation is employed, preferred conditions comprise the use of dimethyl sulphoxide and oxalyl chloride or bromine in a solvent such as dichloromethane or dichlormethane/THF mixtures, at reduced temperature, such as from 0 to −100° C., preferably 50 to −80° C. Preferably, reagents are added at reduced temperature, such as 30 to −80° C., and then once all reagents are added, the reaction mixture is allowed to warm to 15 to 20° C.

Alternatively, the compound of formula (3) may be obtained directly from a compound of formula (1), for example by treatment with dimethysulphoxide and an acid acceptor.

The coupling of the compound of formula (3) with the compound of formula (4) may employ conditions analogous to those given in WO0185702 for the corresponding coupling of a compound of formula (4). Alternatively, conditions comprising refluxing the compounds of formula (3) and (4) in a hydrocarbon solvent, such as toluene or cyclohexane, or mixtures thereof, followed by contact with aqueous acid, such as aqueous HCl may be employed.

Alkyl, aryl, alkoxy or aryloxy groups which may be represented by $R^7$ and $R^8$ include $C_{1-6}$alkyl groups, such as methyl and ethyl groups, $C_{6-12}$aryl groups, such phenyl, tolyl or naphthyl, $C_{1-6}$alkoy groups, such as ethoxy groups, and $C_{6-12}$aryloxy groups such as phenoxy groups.

Anions which may be represented by X include halide.

$R^6$ preferably is $P(=O)R^7R^8$ where $R^7$ and $R^8$ each independently is an alkyl, aryl, alkoxy or aryloxy group, preferably a phenyl group.

When W represents $OP^2$, the protecting group may be removed to form a hydroxy group by methods known in the art for the removal of the given protecting group. For example, silyl protecting groups may be removed by contact with a source of fluoride ion, such as tetrabutylammonium fluoride.

Oxidation of compounds formed by deprotection of compounds wherein W represents $OP^2$ may employ conditions known in the art for the oxidation of pyranols to pyranones, and include those given in "Comprehensive Organic Transformations", R. C. Larock, $2^{nd}$ Ed (1999) p 1670, published by Wiley VCM, incorporated herein by reference. Preferred oxidation systems include $Ag_2CO_3$Celite, especially Celite J2, bromine or Swern.

Ring opening of the compounds of formula (5), when W represent =O or formula (6) may employ conditions known in the art for ring opening of a pyranone. Preferably, the ring is opened by contact with a base, such as sodium hydroxide or calcium oxide. Conveniently, polar solvents are employed, for example methanol, acetonitrile, tetrahydrofuran or mixtures thereof.

Remaining protecting groups may be removed by methods known in the art for the removal of the given protecting group. For example, silyl protecting groups may be removed by contact with a source of fluoride ion, such as tetrabutylammonium fluoride, and benzyl groups may be removed by treatment with TMSI or under selective hydrogenation conditions.

It will also be recognised that compounds of formulae (2), (3) and (5) may also be subjected to oxidation (when W represents —OH) or deprotection and oxidation (when W represents (—O-protecting group) to form the corresponding compound wherein W represents =O.

Preferred compounds of formula (1) are compounds of formula:

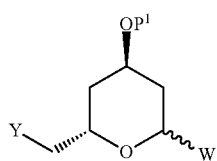

wherein W, P¹ and Y are as previously described.

Preferred compounds of formula (2) are compounds of formula:

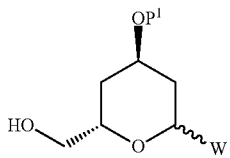

wherein W and P¹ are as previously described.

Preferred compounds of formula (3) are compounds of formula:

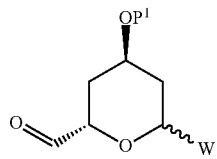

wherein W and P¹ are as previously described.

Preferred compounds of formula (5) are of formula:

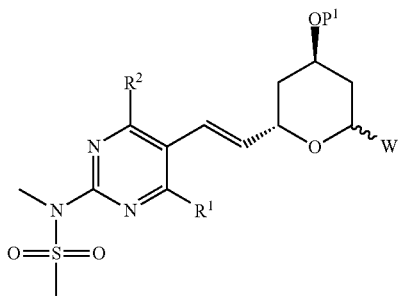

wherein $R^1$, $R^2$, W and $P^1$ are as previously described.

Preferred compounds of formula (6) are of formula:

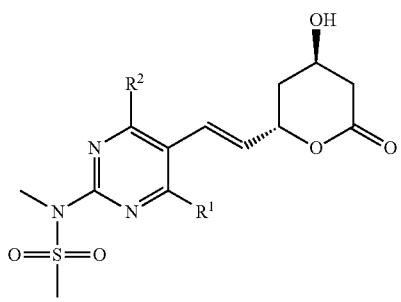

wherein $R^1$ and $R^2$ are as previously described.

Preferred compounds of formula (7) are of formula:

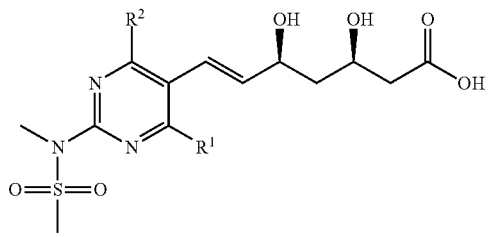

wherein $R^1$ and $R^2$ are as previously described.

Compounds of formula (7) are advantageously converted to pharmaceutically acceptable salts, especially their calcium salts (for example WO0160804).

Compounds of formula (4) are advantageously prepared by the methods given in WO0049014 and WO0185702. Particularly preferred compounds of formula (4) are compounds of formula:

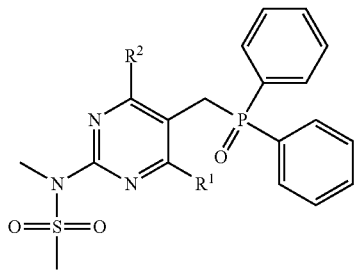

Compounds of formula (1) are advantageously prepared by enzyme catalysed condensation of acetaldehyde and 2-haloacetaldehyde, for example using the method given in U.S. Pat. No. 5,795,749.

Compounds of formulae (2) and (3) and, when W is $OP^2$, formula (5) form further aspects of the present invention.

The invention is illustrated by the following examples.

EXAMPLE 1

Preparation of Chlorolactol methyl acetal ((2S,4R)-2-(chloromethyl)-6-methoxytetrahydro-2H-pyran-4-ol), a compound of Formula 1 where Y=Cl, =H and W=$OP^2$, in which $P^2$=Me Crude chlorolactol (15 g) was dissolved in methanol (150 ml) and heated to 40° C. for 2 hours in the presence of 0.1 ml sulphuric acid. The solvent was removed by rotary evaporation to afford the product as a dark brown flowing oil. The product was dissolved in DCM and washed with sodium bicarbonate solution. The solvent was removed by rotary evaporation to afford the product as a dark brown flowing oil, which was purified by column chromatography (16.1 g) containing a mixture of anomers m/z 179, 149 and 113; $^1$H nmr CDCl₃ 3.6-3.7 (m 2H), 4.1 (m 1H), 1.5-1.6 (m 2H), 4.0 (m 1H), 1.3-1.6 (m 2H), 4.9 (m 1H), 3.3 & 3.5 (s 3H); $^{13}$C nmr CDCl₃ 32, 36, 45, 55&56, 64, 65, 94.

EXAMPLE 2

Preparation of O-benzyl-chlorolactol methyl acetal ((2S,4R)-4-(benzyloxy)-2-(chloromethyl)-6-methoxytetrahydro-2H-pyran), a compound of Formula 1 where Y=Cl, $P^1$=Bn and W=$OP^2$, in which $P^2$=Me Chlorolactol methyl acetal (1 g) was dissolved in THF (5 ml) and charged to sodium hydride (0.33 g 60% in mineral oil) in THF (5 ml) at room temperature. Benzyl bromide (1.9 g) was added dropwise and the mass heated to 80° C. for 2 hours. Methanol (2 ml) was added and the mass was partitioned between DCM water, and was then washed with water. The organic phase was dried and the solvent was removed by rotary evaporation to afford an orange flowing oil (2.1 g), containing a mixture of anomers containing a mixture of anomers. m/z 270; 238; 203; 132; 91; $^1$H nmr $CDCl_3$ 1.6-2.0 (m 4H), 3.4 & 3.5 (s 3H), 3.6 (m 2H), 3.8 (m 1H), 4.0 (m 1H), 4.5 (m 2H), 4.7 (m 1H), 7.3-7.5 (m 5H); $^{13}$C nmr $CDCl_3$ 32&33, 46, 55&56, 53, 66, 74, 96&98, 128-131.

EXAMPLE 3

Preparation of Hydroxy-O-benzyl-lactol methyl acetal ([(2R,4R)-4-(benzyloxy)-6-methoxytetrahydro-2H-pyran-2-yl]methanol), a compound of Formula 2 where P'=Bn and W=$OP^2$, in which $P^2$=Me Preparation of the Acetate Intermediate:

To a 3-liter three necked round bottomed flask flushed with thy nitrogen the O-benzyl-chlorolactol methyl acetal (30 g) was charged into dry N-methyl pyrollidinone (756 mls). Anhydrous tetrabutylammonium acetate (102.57 g) was also charged to the solution. The reaction mixture was then heated at 100° C. for 24 hours. The reaction mixture was sampled at routine intervals and directly analysed by tlc and gc/ms.

The black solution was then diluted with water (150 mls) and extracted with ethyl acetate (3×1500 mls). The combined upper organic layer was then washed with water (3×1500 mls). The aqueous portion showed no product content at this point. The layers were then separated, dried, ($Na_2SO_4$) and the solvent removed in vacuo to yield a black flowing oil (31 g, 95%) containing a mixture of anomers. $^1$H nmr $CDCl_3$ 1.4-1.8 (m 4H), 2.0-2.1 (duplicate s, 3H), 3.4 & 3.5 (s 3H), 3.8 (m 1H), 4.0 (m 1H), 4.1 (m 2H), 4.5 (m, 2H), 4.7-4.9 (m 1H), 7.2-7.3 (m, 5H); $^{13}$C nmr $CDCl_3$ 20.8; 30-35; 55&56; 57&64; 66&68; 69&72; 70&71; 98&99; 127-128 & 138; 170.5; m/z 293, 262, 221, 203, 156, 91 and 43.

Preparation or the Alcohol from the Acetate Intermediate:

To a 5 mls three necked round bottomed flask flushed with dry nitrogen the O-benzyl-chlorolactol methyl acetal acetate (2 g) was charged into dry methanol (10 mls) containing anhydrous potassium carbonate (1 g). The resultant suspension was stirred at 20° C. for 30 minutes. G.C./M.S. showed complete conversion of acetate to alcohol. The solid was filtered off and the solvent removed in vacuo to yield a brown flowing oil containing a mixture of anomers (1.6 g, 93%). $^1$H nmr $CDCl_3$ 1.4-1.8 (m 4H), 3.4 & 3.5 (s 3H), 3.8 (m 1H), 3.9 (m 1H), 4.0 (m 2H), 4.5 (m 2H), 4.7-4.9 (m 1H), 7.2-73 (m, 5H); $^{13}$C nmr $CDCl_3$ 30-38; 55&56; 65&66; 65&69; 70&71; 72&73; 99&100; 128 & 140; m/z 252, 221, 189, 163, 114 and 91.

EXAMPLE 4

Preparation of formyl-O-benzyl-lactol methyl acetal (2S,4R)-4-(benzyloxy)-6-methoxytetrahydro-2H-pyran-2-carbaldehyde a compound of Formula 3 where $P^1$=Bn and W=$OP^2$, in which $P^2$=Me Dess-Martin periodinane reagent (1.91 g) in dichloromethane (50 mls) was charged to a 1000 mls round bottomed flask purged with dry nitrogen. The hydroxy-O-benzyl-lactol methyl acetal (1.0 g,) was dissolved in dichloromethane (50 mls) and added to the Dess-Martin periodinane reagent at 20° C. The reaction mixture was then stirred at room temperature for 30 minutes. The reaction was monitored by tlc. The reaction mixture was then diluted with diethyl ether (500 mls) to precipitate the excess reagent. The suspension was then washed with 10% aqueous sodium hydroxide (200 mls). The upper organic layer was then washed with water (250 mls). The upper organic layer was then separated, dried ($Na_2SO_4$) and the solvent removed in vacuo to yield a dark flowing oil as a mixture of anomers (0.8 g).

$^1$H nmr $CDCl_3$ 1.6-1.9 (m 4H), 3.3 & 3.5 (s 3H), 3.7 (m 1H), 3.8 (m 1H), 4.4 (m 2H), 4.7-4.9 (m 1H), 7.2-8.1 (m, 5H), 9.6-9.7 (2×s, 1H).

$^{13}$C nmr $CDCl_3$ 30-38; 55&56; 65&66; 65&69; 70&71; 99&100; 128 & 140; 201.

m/z 250, 221, 189, 163, 143, 117 and 91.

Alternatively, a Swern oxidation can be carried out as illustrated by the following example:

A stirred solution of oxaiyl chloride (0.037 $cm^3$, 0.44 mmol) in dichloromethane (4 $cm^3$) under nitrogen was cooled to −78 C and DMSO was added in one portion. A solution of the alcohol (100 mg, 0.40 mmol) in dichloromethane (1 $cm^3$) was added to the reaction mixture and the reaction mixture stirred at 78 C for 5 min. Triethylamine (0.272 $cm^3$, 19.8 mmol) was added and the resulting solution was stirred at 78 C for 25 min and used immediately without isolation or purification. Tlc $r_f$ 0.40 ethyl acetate:hexane (1:1) orange spot with 2,4-dinitrophenylhydrazine stain

EXAMPLE 5

Preparation of Pyrimidyl-ethenyl-O-benzyl-lactol methyl acetal, a compound of Formula 5 where $R^1$=iPr, $R^2$=4-$FC_6H_4$, $R^3$=Me, $R^4$=$SO_2$Me, $P^1$=Bz and W=$OP^2$, in which $P^2$=Me.

Pyrimidyl-ethenyl-O-benzyl-lactol methyl acetal was obtained by first dissolving 0.21 g of the compound of formula 4 wherein $R^3$=Me, $R^4$=$SO_2$Me and $R^6$=$PO(Ph)_2$ in 10 ml dry THF, cooling to −60° C. and then adding 0.2 ml of a 2M solution of sodium hexamethyldisilazide. After 20 min, a solution of 0.1 g formyl-O-benzyl-lactol methyl acetal in 10 ml dry THF at −30° C. was added. The reaction mixture was then maintained at this temperature for 8 hours and monitored by tlc. The reaction mixture was allowed to slowly warm up to 20° C. Glacial acetic (5 mls) acid was then charged to quench the reaction. Water (5 mls) was also charged to the mixture. The solvent was then removed in vacuo and reconstituted with toluene (15 mls) and water (15 mls). The upper organic layer was then separated and the aqueous layer was then washed with ethyl acetate (15 mls). The combined organics were then dried and the solvent removed in vacuo to yield an oil containing a mixture of isomers, that can be purified by chromatography. The desired product had the tentative NMR assignment $^1$H nmr CDCl$_3$ 1.2 (d, 6H), 1.6-1.9 (m 4H), 3.3 (s, 3H), 3.4 (s, 3H), 3.2 & 3.5 (2×s, 3H), 3.7 (m 1H), 3.8 (m 1H), 4.2 (m 1H), 4.4 (m 2H), 4.7-4.9 (m 1H), 5.35 (dd, 1H), 5.85-6.7 (d, 1H), 7.1-8.1 (m, 9H).

EXAMPLE 6

Preparation of Pyrimidyl-ethenyl-OH-lactol methyl acetal (Rosuvastatin Lactol-OMe) a compound of Formula 5 where R$^1$=iPr, R$^2$=4-FC$_6$H$_4$, R$^3$=Me, R$^4$=SO$_2$Me, P$^1$=H and W=OP$^2$, in which P$^2$=Me Pyrimidyl-ethenyl-OH-lactol methyl acetal may be obtained by reaction of Pyrimidyl-ethenyl-O-benzyl-lactol methyl acetal with TMSI.

EXAMPLE 7

Preparation of Pyrimidyl-ethenyl-OH-lactol (Rosuvastatin Lactol), a compound of Formula 5 where R$^1$=iPr, R$^2$=4-FC$_6$H$_4$, R$^3$=Me, R$^4$=SO$_2$Me, P$^1$=H and W=OP$^2$, in which P$^2$=H Pyrimidyl-ethenyl-OH-lactol may be obtained by treatment of the Pyrimidyl-ethenyl-OH-lactol methyl acetal with 0.1N HCl in methanol.

EXAMPLE 8

Preparation of Lactone, a compound of Formula 6 where R$^1$=iPr, R$^2$=4-FC$_6$H$_4$, R$^3$=Me, R$^4$=SO$_2$Me, P$^1$=H The pyrimidyl-ethenyl-OH-lactol (35 mg, 0.065 mmol) in dichloromethane (0.5 ml) was added to Dess-Martin periodinane (30 mg, 0.07 mmol) and stirred at room temperature for 2.5 hours. The reaction was partitioned between 1M sodium hydroxide and diethyl ether. The phases were then separated and the organic volume reduced in vaccuo to afford the crude product oil.

EXAMPLE 9

Preparation of Rosuvastatin (hydrolysis of Lactone), a compound of Formula 7 where R$^1$iPr, R$^2$=4-FC$_6$H$_4$, R=Me, R$^4$=SO$_2$Me The lactone (1.1 g) was dissolved in ethanol (10 ml). Water (2 ml) and Ca(OH)$_2$ (0.15 g) were added and the suspension warmed to 60° C. for 3 hours. A further 10 ml of warm water was added, then the mixture allowed to cool slowly to room temperature. The precipitate formed was filtered and dried to give Rosuvastatin calcium salt. The material was identical to an authentic sample by mixed melting point, NMR and mass spectrometry.

The invention claimed is:

1. A process for the preparation of a compound of formula (5)

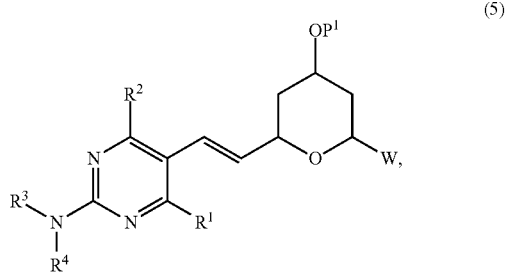

comprising coupling a compound of formula (3)

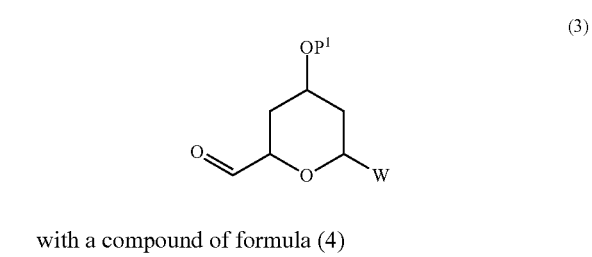

with a compound of formula (4)

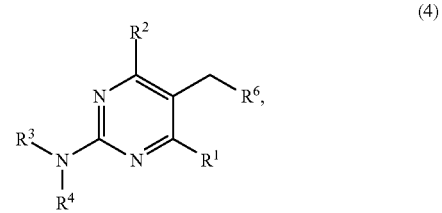

wherein:
R$^1$ represents an alkyl group;
R$^2$ represents an aryl group;
R$^3$ represents a protecting group or an alkyl group;
R$^4$ represents a protecting group or a SO$_2$R$^5$ group where R$^5$ is an alkyl group;
R$^6$ represents (PR$^7$R$^8$)$^+$X$^-$ or P(=O)R$^7$R$^8$ in which X is an anion and R$^7$ and R$^8$ each independently is an alkyl, aryl, alkoxy, or aryloxy group;
P$^1$ represents hydrogen or a protecting group; and
W represents —OP$^2$, in which P$^2$ represents hydrogen or a protecting group.

2. A compound of formula (5)

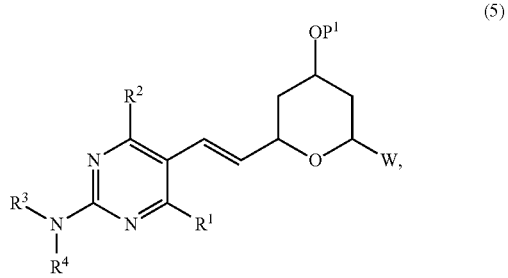

wherein:
R$^1$ represents an alkyl group;
R$^2$ represents an aryl group;

R³ represents hydrogen, a protecting group, or an alkyl group;

R⁴ represents a protecting group or a $SO_2R^5$ group where $R^5$ is an alkyl group;

P¹ represents hydrogen or a protecting group; and

W represents —$OP^2$, in which P² represents hydrogen or a protecting group.

3. The process of claim 1, wherein each of R⁷ and R⁸ is a phenyl group.

4. The process of claim 1, wherein R¹ represents a $C_{1-6}$ alkyl group.

5. The process of claim 4, wherein R¹ represents an isopropyl group.

6. The process of claim 1, wherein R² is 4-fluorophenyl group.

7. The process of claim 1, wherein R³ represents a $C_{1-6}$ alkyl group.

8. The process of claim 1, wherein R³ represents a methyl group.

9. The process of claim 1, wherein R⁵ is a $C_{1-6}$ alkyl group.

10. The process of claim 9, wherein R⁵ is a methyl group.

11. The process of claim 1, wherein P¹ represents hydrogen or a protecting group selected from the group consisting of tetrahydropyranyl, benzyl, methyl, silyl, and benzoyl.

12. The process of claim 1, wherein P² represents a protecting group selected from the group consisting of tetrahydropyranyl, benzyl, methyl, silyl, and benzoyl.

13. The compound of claim 2, wherein R¹ represents a $C_{1-6}$ alkyl group.

14. The compound of claim 13, wherein R¹ represents an isopropyl group.

15. The compound of claim 2, wherein R² is 4-fluorophenyl group.

16. The compound of claim 2, wherein R³ represents a $C_{1-6}$ alkyl group.

17. The compound of claim 2, wherein R³ represents a methyl group.

18. The compound of claim 2, wherein R⁵ is a $C_{1-6}$ alkyl group.

19. The compound of claim 18, wherein R⁵ is a methyl group.

20. The compound of claim 2, wherein P¹ represents hydrogen or a protecting group selected from the group consisting of tetrahydropyranyl, benzyl, methyl, silyl, and benzoyl.

21. The compound of claim 2, wherein P² represents a protecting group selected from the group consisting of tetrahydropyranyl, benzyl, methyl, silyl, and benzoyl.

\* \* \* \* \*